(12) United States Patent
Miyashita et al.

(10) Patent No.: US 6,589,409 B2
(45) Date of Patent: Jul. 8, 2003

(54) MULTILAYERED GAS SENSING ELEMENT EMPLOYABLE IN AN EXHAUST SYSTEM OF AN INTERNAL COMBUSTION ENGINE

(75) Inventors: Akira Miyashita, Handa (JP); Akio Tanaka, Gifu (JP); Toshitaka Saito, Toyohashi (JP); Keigo Mizutani, Okazaki (JP)

(73) Assignees: Denso Corporation (JP); Nippon Soken, Inc. (JP)

( * ) Notice: Subject to any disclaimer, the term of this patent is extended or adjusted under 35 U.S.C. 154(b) by 70 days.

(21) Appl. No.: 09/821,807

(22) Filed: Mar. 30, 2001

(65) Prior Publication Data
US 2001/0025789 A1 Oct. 4, 2001

(30) Foreign Application Priority Data

Mar. 31, 2000 (JP) .......................... 2000-098049
Mar. 22, 2001 (JP) .......................... 2001-083501

(51) Int. Cl.[7] ............................................ G01N 27/407
(52) U.S. Cl. ..................... 204/425; 204/408; 204/426; 204/427
(58) Field of Search ........................ 204/408, 421–429

(56) References Cited

U.S. PATENT DOCUMENTS

| | | | |
|---|---|---|---|
| 4,882,033 A | * | 11/1989 | Shibata et al. |
| 5,866,799 A | | 2/1999 | Kato et al. |
| 5,879,525 A | * | 3/1999 | Kato |
| 6,274,016 B1 | * | 8/2001 | Hasei et al. |
| 6,319,377 B1 | * | 11/2001 | Hasei et al. |
| 6,383,354 B1 | * | 5/2002 | Kurokawa et al. |

FOREIGN PATENT DOCUMENTS

JP        2885336        2/1999

* cited by examiner

Primary Examiner—T. Tung
(74) Attorney, Agent, or Firm—Nixon & Vanderhye PC

(57) ABSTRACT

An objective gas to be measured is introduced into first and second chambers which are connected via a diffusion resistive passage. A first electrochemical cell is provided in the first chamber for pumping in and out oxygen in accordance with an applied voltage. A second electrochemical cell is provided in the second chamber and responsive to application of a predetermined voltage for generating a sensor current representing a specific gas concentration in the objective gas. The first electrochemical cell is located between the first chamber and a reference gas chamber so that oxygen pumping in and out operation can be performed between the first chamber and the reference gas chamber.

16 Claims, 14 Drawing Sheets

MULTILAYERED GAS SENSING ELEMENT EMPLOYABLE IN AN EXHAUST SYSTEM OF AN INTERNAL COMBUSTION ENGINE

BACKGROUND OF THE INVENTION

The present invention relates to a multilayered gas sensing element capable of detecting a specific gas (such as NOx) concentration and preferably employable in an exhaust system for an internal combustion engine of an automotive vehicle.

Harmful gases emitted from automotive internal combustion engines cause serious air pollution the modem society now faces. Various laws and regulations require automotive manufacturers to satisfy severe standards for promoting purification of emission gases. Under such circumferences, it is known that the emission gas purification can be effectively performed by directly detecting the NOx concentration to feedback control the engine combustion as well as to monitor the catalyst condition based on the detected NOx value.

FIG. 17 shows a conventional multilayered gas sensing element 9 which is installable in the exhaust system of an automotive internal combustion engine and is capable of detecting the NOx concentration in the exhaust gas.

The multilayered gas sensing element 9 comprises solid electrolytic sheets 963 and 965 and insulating sheets 964 and 966 stacked to form a first chamber 911 and a second chamber 912 into which an objective gas to be measured is introduced.

A first diffusion resistive passage 910 connects the first chamber 911 to an outside of the gas sensing element 9. A second diffusion resistive passage 920 connects the first chamber 911 to the second chamber 912. Furthermore, the multilayered gas sensing element 9 comprises a reference gas chamber 914 into which a reference gas is introduced.

A first electrochemical cell 902, located or provided in the first chamber 911, pumps in and out oxygen in accordance with an applied voltage. A second electrochemical cell 903, located or provided in the second chamber 912, is responsive to application of a predetermined voltage for generating a sensor current representing a NOx concentration in the objective gas.

The second electrochemical cell 903 has an electrode on which NOx is reducible. Therefore, the NOx concentration can be measured based on an ion current caused by the reduction of NOx.

Accordingly, when excessive oxygen resides in the second chamber 912 and the oxygen concentration is fluctuating, the second electrochemical cell 903 produces an sensor output corresponding to a sum of NOx concentration and fluctuating oxygen concentration in the second chamber 912. Thus, the NOx concentration detected by the second electrochemical cell 903 is inaccurate.

To solve this problem, the first electrochemical cell 902 is provided on the surface of the first chamber 911. The first electrochemical cell 902 discharges oxygen from the first chamber 911 to the outside of the gas multilayered sensing element 9 so as to maintain the oxygen concentration in the first and second chambers 911 and 912 to a constant level.

However, according to the above-described conventional multilayered gas sensing element, when the air-fuel ratio of the exhaust gas to be measured is shifted to the rich side, it is necessary to introduce oxygen into the first chamber 911 to oxidize the reducible gas, such as propane, contained in the measured exhaust gas. However, one of the electrodes of the first electrochemical cell 902 is not brought into contact with the reference gas in the reference gas chamber 914. This makes it impossible to detect the air-fuel ratio being switched to the rich side. Hence, the first electrochemical cell 902 cannot function properly in the rich side of air-fuel ratio.

Furthermore, in this case, the inside of second chamber 912 is filled by a rich environment. An inverse electromotive force is applied to the second electrochemical cell 903. This makes it impossible to detect the NOx concentration.

Similar problem will arise in general multilayered sensing elements having a sensing mechanism for detecting a specific gas concentration based on an ion current caused in response to oxygen ion caused when the specific gas is decomposed on the electrode of the second electrochemical cell.

SUMMARY OF THE INVENTION

To solve the above-described problems, an object of the present invention is to provide a multilayered gas sensing element capable of accurately detecting a specific gas concentration of an exhaust gas emitted from an automotive engine even when combustion condition changes so widely that the air-fuel ratio changes in a wide range from a lean side to a rich side.

In order to accomplish the above and other related objects, the present invention provides a multilayered gas sensing element comprising first and second chambers into which an objective gas to be measured is introduced, a first diffusion resistive passage connecting the first chamber to an outside of the gas sensing element, a second diffusion resistive passage connecting the first chamber to the second chamber, a first electrochemical cell having one end located in the first chamber and the other end provided in a reference gas chamber for pumping in and out oxygen in accordance with an applied voltage, and a second electrochemical cell having one end located in the second chamber and being responsive to application of a predetermined voltage for generating a sensor current representing a specific gas concentration in the objective gas.

The multilayered gas sensing element of the present invention is characterized in that the first electrochemical cell has one end located in the first chamber and the other end provided in the reference gas chamber and the second electrochemical cell has one end located in the second chamber.

The multilayered gas sensing element of the present invention functions in the following manner.

The first electrochemical cell faces both the first chamber and the reference gas chamber.

When the air-fuel ratio is shifted to the rich side, such switching of air-fuel ratio can be detected as the one end of the first electrochemical cell is located in the reference gas chamber. Accordingly, the first electrochemical cell can pump oxygen into the first chamber.

Furthermore, pumping operation of the first electrochemical cell makes it possible to maintain the oxygen concentration in the second chamber to a constant level. Accordingly, no inverse electromotive force is applied to the second electrochemical cell. This makes it possible to measure a specific gas concentration of the measured gas in a wide range from the lean side to the rich side.

As apparent from the foregoing, the present invention provides a multilayered gas sensing element capable of accurately detecting a specific gas concentration in a measured gas exhausted from an internal combustion engine even if combustion condition is controlled with the air-fuel ratio varying in a wide range from the lean side to the rich side.

Furthermore, according to the multilayered gas sensing element of the present invention, the oxygen pumping in and out operation causes an oxygen ion current flowing in an electric circuit of the first electrochemical cell.

The oxygen ion current has a current value representing the air-fuel ratio. Therefore, the first electrochemical cell can be used as an air-fuel ratio detecting cell.

In other words, the multilayered gas sensing element of the present invention can measure both the specific gas concentration and the air-fuel ratio simultaneously.

Application of the multilayered gas sensing element of the present invention is not limited to measurement of NOx concentration. Therefore, the multilayered gas sensing element of the present invention is applicable to other types of gas sensors, such as a CO sensor and a HC sensor.

Furthermore, according to the present invention, it is preferable that the second electrochemical cell has the other end located in the reference gas chamber.

This arrangement is effective to stabilize an electric potential of the positive electrode side of the second electrochemical cell. Thus, the specific gas concentration is accurately detectable.

Furthermore, it is preferable that the reference gas chamber for the second electrochemical cell is formed separately from the reference gas chamber for the first electrochemical cell.

According to this arrangement, even when the oxygen concentration in the reference gas chamber of the first electrochemical cell varies due to the pumping function, such variation is not transmitted to the reference gas chamber of the second electrochemical cell. Thus, the specific gas concentration is accurately detectable.

Furthermore, according to the present invention, it is preferable that the multilayered gas sensing element further comprises a heater incorporating a heat generating element capable of generating heat in response to current applied thereto, and an ion current path between the second electrochemical cell and the heat generating element is longer than an ion current path between the first electrochemical cell and the heater generating element.

In general, to assure accurate measurement of a specific gas concentration by the multilayered gas sensing element, it is necessary to quickly and sufficiently warm up the second electrochemical cell to its activation temperature. To this end, the multilayered gas sensing element is generally equipped with an electrically operable heater having a built-in heat generating element.

Electric power supplied to the heat generating element is very large compared with the sensor output level of the second electrochemical cell and therefore becomes a noise source giving adverse influence to the sensor output signal.

Electric power is also supplied to the first electrochemical cell. However, even if the current flowing across the first electrochemical cell contains a significant noise due to influence of power supply to the heat generating element, the output of the first electrochemical cell will not be so badly influenced because the first electrochemical cell is arranged to perform pumping of oxygen and the pumping performance is not so influenced by the current flowing therethrough.

Accordingly, to assure accurate measurement of the specific gas concentration, the ion current path between the second electrochemical cell and the heat generating element is set to be longer than the ion current path between the first electrochemical cell and the heater generating element.

The ion current path defined in this invention represents a current path along which the oxygen ion current can flow. Usually, the ion current path is a shortest path developed along an electrically conductive route, such as a solid electrolytic sheet, of the multilayered gas sensing element.

Furthermore, according to the present invention, it is preferable that the heater has a base material made of alumina.

Alumina is an insulating materia. The power current supplied to the heat generating element can be effectively prevented from flowing into other portion of the multilayered sensor element. Thus, the first and second electrochemical cells are not adversely influenced by the power current to the heat generating element. No noise is involved in the sensor output.

Furthermore, according to the present invention, it is preferable that an insulating resistance between the second electrochemical cell and the heat generating element is larger than an insulating resistance between the first electrochemical cell and the heat generating element. It is also preferable that a minium distance between the second electrochemical cell and the heat generating element is longer than a minimum distance between the first electrochemical cell and the heat generating element.

Electric power supplied to the heat generating element is very large compared with the sensor output level of the second electrochemical cell and therefore becomes a noise source giving adverse influence to the sensor output signal. On the other hand, even if the current flowing across the first electrochemical cell contains a significant noise due to influence of power supply to the heat generating element, the output of the first electrochemical cell will not be so badly influenced by the same reason described above.

Accordingly, to suppress the adverse influence of the heat generating element, the insulating resistance between the second electrochemical cell and the heat generating element is set to be larger than the insulating resistance between the first electrochemical cell and the heater generating element, thereby ensuring accurate measurement of the specific gas concentration, From the similar reason, the minimum distance between the second electrochemical cell and the heat generating element is set to be longer than the minimum distance between the first electrochemical cell and the heater generating element, thereby ensuring accurate measurement of the specific gas concentration.

Furthermore, according to the present invention, it is preferable that the insulating resistance between the second electrochemical cell and the heat generating element is equal to or larger than $1 \times 10^{-12}$ Ω, leak current between the second electrochemical cell and the heat generating element is equal to or smaller than $2 \times 10^{-11}$ A, and the minium distance between the second electrochemical cell and the heat generating element is equal to or larger than 0.4 mm.

Satisfying all of the above-described conditions will assure the accurate measurement of the specific gas concentration.

If the insulating resistance is smaller than $1 \times 10^{12}$ Ω, a significant leak current will flow from the heat generating element to the second electrochemical cell and therefore the output signal of the second electrochemical cell will contain a noise component. Thus, the sensor output will become inaccurate.

The leak current is a current flowing from the heat generating element to the second electrochemical cell. If the leak current exceeds $2\times10^{-11}$ A, the output signal of the second electrochemical cell will contain a noise component. Thus, the sensor output will become inaccurate.

When the minium distance is smaller than 0.4 mm, the output signal of the second electrochemical cell will contain a noise component. Thus, the sensor output will become inaccurate.

It is preferable that an upper limit of the minimum distance is 10 mm. If the minimum distance exceeds 10 mm, a thermal capacity of the sensor element will become so large that it will take a long time for each electrochemical cell to reach an active temperature after activation of the heater.

Furthermore, according to the present invention, it is preferable that the first electrochemical cell comprises a pair of electrodes provided on opposite surfaces of a first solid electrolytic sheet, and the second electrochemical cell comprises a pair of electrodes provided on opposite surfaces of a second solid electrolytic sheet which is different from the first solid electrolytic sheet.

The voltage applied to the first electrochemical cell is larger than the output level of the second electrochemical cell. Thus, to reduce or eliminate adverse influence of the voltage applied to the first electrochemical cell, the second electrochemical cell is provided on the solid electrolytic sheet different and spaced from the solid electrolytic sheet of the first electrochemical cell, thereby ensuring accurate measurement of the specific gas concentration.

Furthermore, according to the present invention, it is preferable that an alumina sheet is disposed between the first electrochemical cell and the second electrochemical cell. This arrangement is effective to prevent the leak current from flowing from the first electrochemical cell to the second electrochemical cell or vice versa, thereby ensure the accurate detection of the specific gas concentration.

Furthermore, according to the present invention, it is preferable that a third electrochemical cell is provided to measure an oxygen concentration in one of the first chamber and the second chamber.

In this case, in addition to measurement of the specific gas concentration (e.g., NOx concentration), the oxygen concentration is measured in either the first chamber or the second chambers. Thus, it becomes possible to maintain the oxygen concentration in at least one of first and second chambers to a constant level. Hence, the measuring accuracy of the specific gas concentration by the second electrochemical cell can be further ensured.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Figure 1:
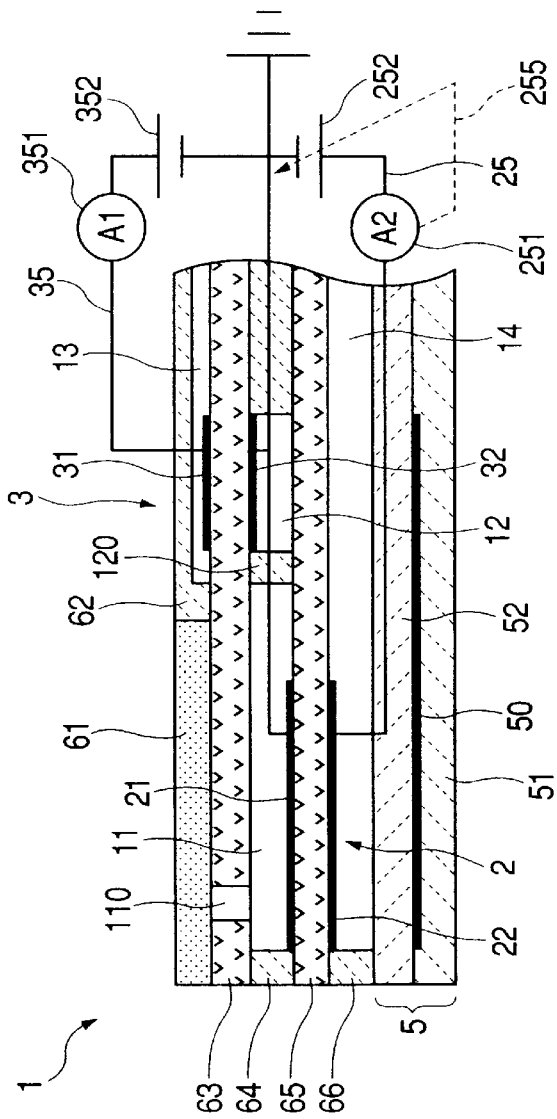
FIG. 1 is a cross-sectional view showing a multilayered gas sensing element in accordance with a first embodiment of the present invention.

Preferred embodiments of the present invention will be explained hereinafter with reference to attached drawings. Identical parts are denoted by the same reference numerals throughout the drawings.

First Embodiment

A multilayered gas sensing element of a first embodiment will be explained with reference to FIGS. 1 to 6.

A multilayered gas sensing element 1 of the first embodiment comprises two chamber, i.e., a first chamber 11 and a second chamber 12, into which an objective gas to be measured is introduced. A first diffusion resistive passage 110 connects the first chamber 11 to an outside of the gas sensing element 1. A second diffusion resistive passage 120 connects the first chamber 11 to the second chamber 12. Furthermore, the multilayered gas sensing element 1 comprises a first reference gas chamber 14 and a second reference gas chamber 13 into which a reference gas is introduced.

A first electrochemical cell 2, located or provided on a surface defining the first chamber 11, pumps in and out oxygen in accordance with an applied voltage. A second electrochemical cell 3, located or provided on a surface defining the second chamber 12, is responsive to application of a predetermined voltage for generating a sensor current representing a NOx concentration in the objective gas.

The first electrochemical cell 2 is provided between the first chamber 11 and the first reference gas chamber 14, so that oxygen pumping in and out operation can be performed between the first chamber 11 and the first reference gas chamber 14.

The multilayered gas sensing element 1 is incorporated in a gas sensor (not shown) installed in an exhaust pipe (not shown) of an automotive engine (not shown) to measure a NOx concentration in the exhaust gas for the purposes of controlling engine combustion and monitoring an exhaust gas purification catalyst.

As shown in FIG. 1, the multilayered gas sensing element 1 of the first embodiment comprises a first solid electrolytic sheet 63, a first insulating sheet 64, a second solid electrolytic sheet 65, a second insulating sheet 66, and a ceramic heater 5 which are successively stacked in this order so as to constitute an integrated body of the multilayered gas sensing element 1.

Furthermore, the multilayered gas sensing element 1 comprises a porous sheet 61 and an insulating spacer 62 both covering an outer surface of the first solid electrolytic sheet 63. The porous sheet 61 covers an inlet of the first diffusion resistive passage 110. The objective gas flowing in the exhaust pipe is appropriately decelerated and diffused in the porous sheet 61 and then introduced in the first chamber 11 via the first diffusion resistive passage 110.

Figure 2:
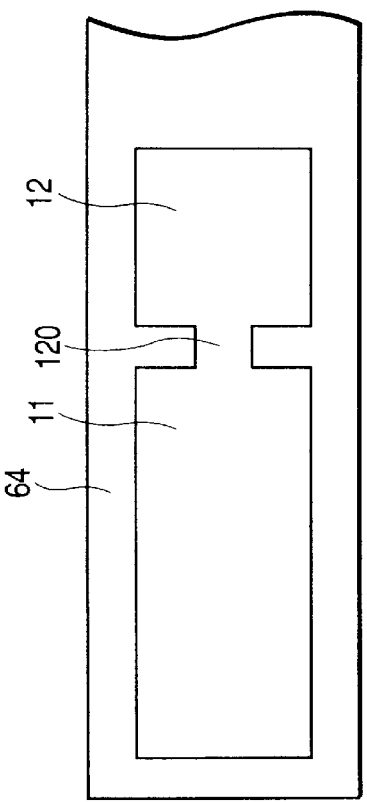
FIG. 2 is a plan view showing an insulating sheet defining first and second chambers for introducing an objective measured gas, constituting part of the multilayered gas sensing element shown in FIG. 1.

As shown in FIG. 2, the first chamber 11 and the second chamber 12 are defined in the first insulating sheet 64 interposed between the first solid electrolytic sheet 63 and the second solid electrolytic sheet 65. The first chamber 11 and the second chamber 12 are connected via the second diffusion resistive passage 120 which is a narrow passage capable of adequately decelerating the gas flowing between the first chamber 11 and the second chamber 12.

The second reference gas chamber 13 is defined by an inner recess of the insulating spacer 62 closed by the outer surface of the first solid electrolytic sheet 63. The first reference gas chamber 14 is defined in the second insulating sheet 66 interposed between the second solid electrolytic sheet 65 and the ceramic heater 5.

The heater 5 comprises a heater substrate 51, a heat generating element 50 generating heat in response to supply of electric power, and a coating substrate 52. Both of the heater substrate 51 and the coating substrate 52 are insulating members.

The first solid electrolytic sheet 63 and the second solid electrolytic sheet 65 are oxygen ion conductive zirconia substrates. The rest, i.e., the insulating spacer 62, the first insulating sheet 64, the second insulating sheet 66, and the heater substrate 51 are all alumina substrates. The porous sheet 61 is an alumina substrate having a higher porosity.

The first electrochemical cell 2 comprises a pair of electrodes 21 and 22 located or provided on opposite (i.e., upper and lower) surfaces of the second solid electrolytic sheet 65 interposed between the first chamber 11 and the first reference gas chamber 14.

The second electrochemical cell 3 comprises a pair of electrodes 31 and 32 located or provided on opposite (i.e., upper and lower) surfaces of the first solid electrolytic sheet 63 interposed between the first chamber 11 and the second reference gas chamber 13.

The electrode 21 is inactive against NOx and therefore has no capability of decomposing NOx. On the other hand, the electrode 32 is active against NOx and therefore decomposes NOx into oxygen ions and nitrogen ion.

The first electrochemical cell 2 is connected to an ammeter 251 and a power source 252 so as to constitute a pump circuit 25. A feedback circuit 255 is provided between the ammeter 251 and the power source 252. The feedback circuit 255 controls the voltage of power source 252 based on a current value of the ammeter 251, thereby causing the first electrochemical cell 2 to perform the oxygen pumping in and out operation.

Furthermore, the second electrochemical cell 3 is connected to an ammeter 351 and a power source 352 so as to constitute a sensor circuit 35. The ammeter 351 measures an oxygen ion current flowing across the second electrochemical cell 3. The oxygen ion current is proportional to a NOx concentration. Thus, the NOx concentration can be known from the measured current value of ammeter 351. A negative terminal of the power source 252 in the pump circuit 25 and a negative terminal of the power source 352 in the sensor circuit 35 are both grounded.

Next, performance evaluation of the multilayered gas sensing element 1 of the first embodiment will be explained.

For evaluation test, the multilayered gas sensing element 1 was installed on a practical automotive engine to expose the multilayered gas sensing element 1 to an actual exhaust gas environment. The second electrochemical cell current was measured by the ammeter 351.

According to the test result, output characteristics of the multilayered gas sensing element 1 was stable irrespective of change of air-fuel ratio, i.e., rich (A/F<14.5), stoichiometric (A/F=14.5), and lean (A/F>14.5), of the exhaust gas.

Figure 4:
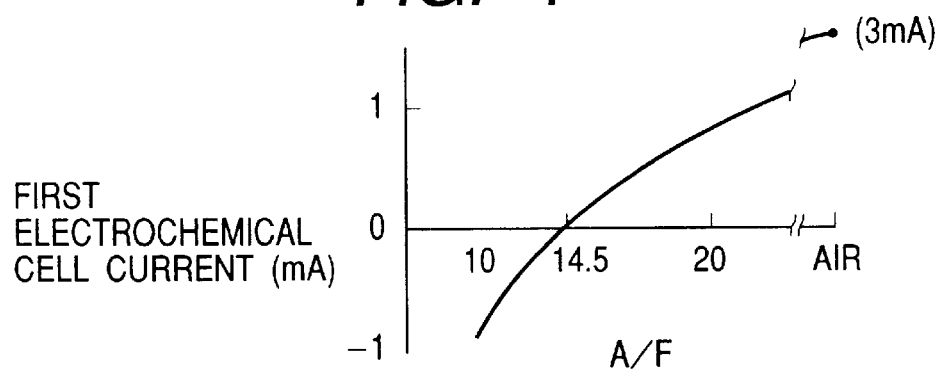
FIG. 4 is a graph showing relationship between air-fuel ratio and first electrochemical cell current obtained from the multilayered gas sensing element in accordance with the first embodiment of the present invention.

FIG. 4 shows measuring result of the first electrochemical cell current measured by the ammeter 251. As understood from FIG. 4, the air-fuel ratio (A/F) of the objective gas can be known from the first electrochemical cell current measured by the ammeter 251.

Figure 3:
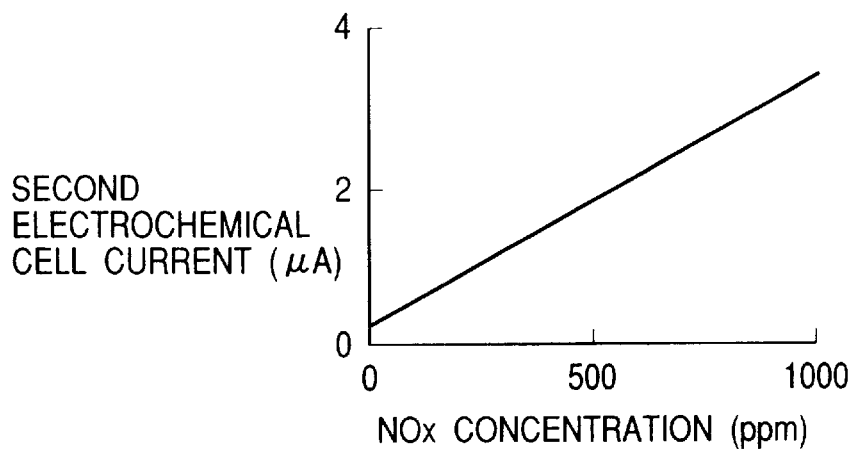
FIG. 3 is a graph showing relationship between NOx concentration and second electrochemical cell current obtained from the multilayered gas sensing element in accordance with the first embodiment of the present invention.

FIG. 3 shows measuring result of the second electrochemical cell current measured by the ammeter 351 when the tested engine was driven with a rich air-fuel ratio (A/F=12) while the NOx concentration in the exhaust gas was changed from 0 to 1,000 ppm. As understood from FIG. 3, the NOx concentration of the objective gas can be known from the second electrochemical cell current measured by the ammeter 351. Thus, the multilayered gas sensing element 1 can detect the NOx concentration of the objective gas.

Figure 17:
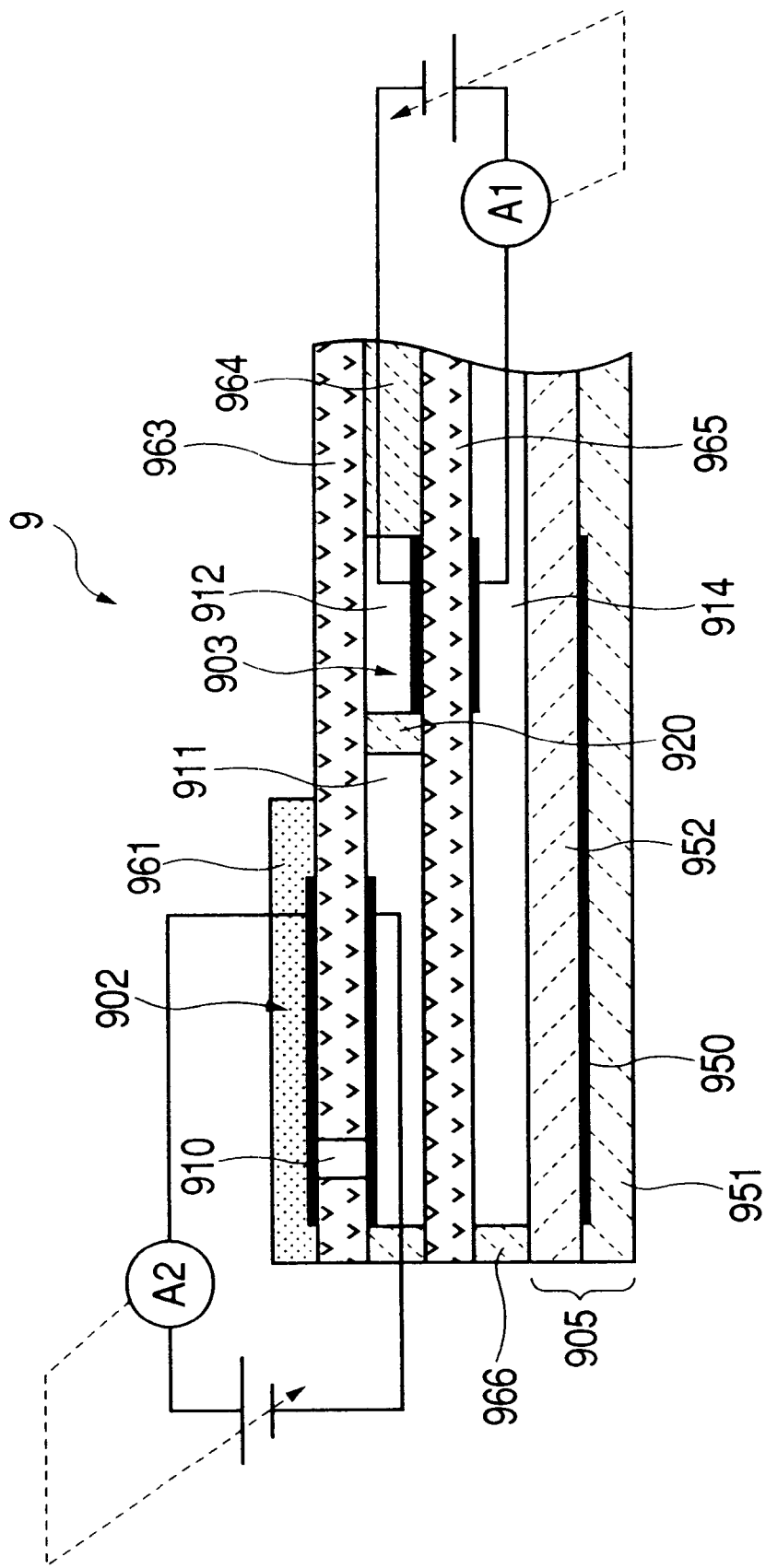
FIG. 17 is a cross-sectional view showing a conventional multilayered gas sensing element.

The conventional multilayered gas sensing element 9 shown in FIG. 17 is different from the multilayered gas sensing element 1 of the first embodiment in that the first electrochemical cell 902 is disposed between the first chamber 911 and the outside of the gas sensing element 9 while the second electrochemical cell 903 is disposed between the second chamber 912 and the reference gas chamber 914.

The conventional multilayered gas sensing element 9 was also tested in the same condition. When the air-fuel ratio was shifted to the rich side, the inside of the second chamber 912 was filled by in a rich environment. Thus, an inverse electromotive force was applied to the second electrochemical cell 903. As a result, the NOx concentration could not be measured.

Figure 5:
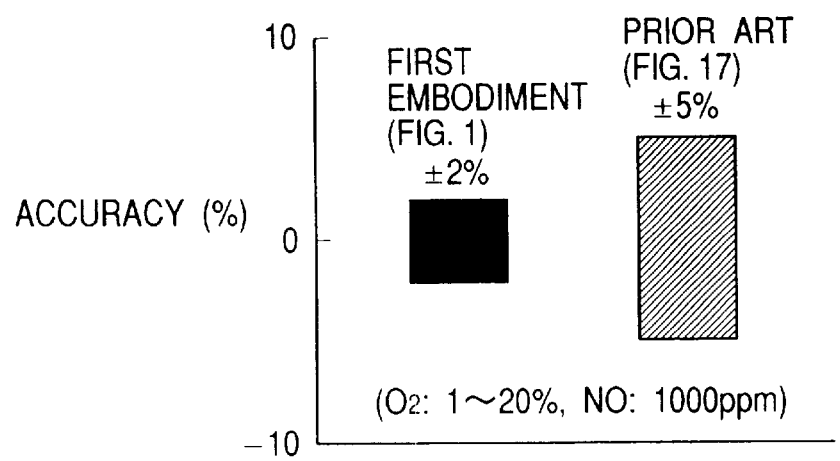
FIG. 5 is a graph showing sensing accuracy of the multilayered gas sensing element in accordance with the first embodiment of the present invention in comparison with that of a conventional gas sensing element.

FIG. 5 shows measuring result of the NOx concentration obtained when the multilayered gas sensing element 1 shown in FIG. 1 and the conventional multilayered gas sensing element 9 shown in FIG. 17 were exposed in a model gas containing 1–20% oxygen (O2) and 1,000 ppm nitrogen oxygen (NO).

As understood from FIG. 5, the multilayered gas sensing element 1 of the first embodiment has excellent measuring accuracy compared with that of the conventional multilayered gas sensing element 9.

The multilayered gas sensing element 1 of the first embodiment functions in the following manner.

According to the first embodiment, the first electrochemical cell 2 is disposed between the first chamber 11 and the first reference gas chamber 14, so that oxygen pumping in and out operation can be performed between the first chamber 11 and the first reference gas chamber 14.

When the air-fuel ratio of the objective gas is shifted to the rich side, an electromotive force is generated in accordance with an oxygen concentration difference between the first chamber 11 and the first reference gas chamber 14. Considering the electromotive force thus produced, the voltage applied to the first electrochemical cell 2 can be controlled to pump in and out the oxygen between the first reference gas chamber 14 and the first chamber 11. The oxygen pumping in and out operation is thus continuously performed even if the air-fuel ratio is not lean.

As a result, when the air-fuel ratio is rich, the oxygen concentration in the first chamber 11 and the second chamber 12 can be maintained at a constant level. No inverse electromotive force is applied to the second electrochemical cell 3. Thus, it becomes possible to accurately detect the NOx concentration of the exhaust gas in a wide range of the air-fuel ratio varying from the lean side to the rich side.

As apparent from FIG. 1, the multilayered gas sensing element 1 comprises the heater 5 integrally formed with the first electrochemical cell 2 and the second electrochemical cell 3. An ion current path between second electrochemical cell 3 and the heat generating element 50 of the heater 5 is longer than an ion current path between the first electrochemical cell 2 and the heat generating element 50.

This arrangement is advantageous in that the second electrochemical cell 3 is not adversely influenced by electric power supply to the heat generating element 50. Thus, the first embodiment provides an excellent multilayered gas sensing element capable of accurately measuring the specific gas (e.g., NOx) concentration.

Furthermore, according to the multilayered gas sensing element 1 shown in FIG. 1, the second electrochemical cell 3 and the first electrochemical cell 2 are formed or provided on different solid electrolytic sheets.

This arrangement is advantageous in that the second electrochemical cell 3 is not adversely influenced by leak current caused by the voltage applied to the first electrochemical cell 2. Thus, the multilayered gas sensing element of the first embodiment can ensure accurate measurement of the specific gas (e.g., NOx) concentration.

Second Embodiment

Figure 6:
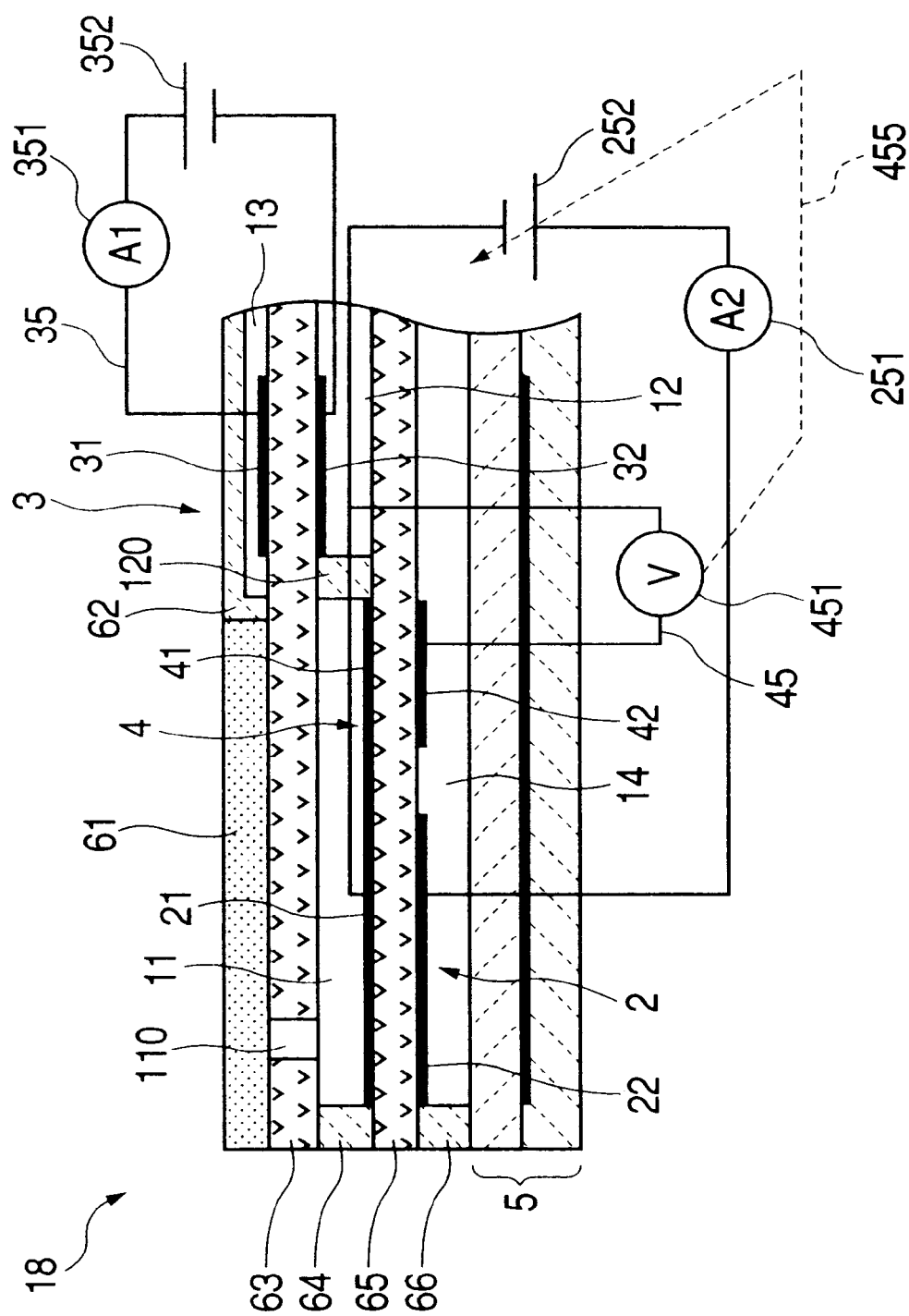
FIG. 6 is a cross-sectional view showing a multilayered gas sensing element in accordance with a second embodiment of the present invention.

FIG. 6 shows a multilayered gas sensing element having a third electrochemical cell.

As shown in FIG. 6, a multilayered gas sensing element 18 of the second embodiment comprises a third electrochemical cell 4 located or provided between the first chamber 11 and the first reference gas chamber 14. More specifically, the third electrochemical cell 4 comprises a pair of electrodes 41 and 42 located or provided on opposite (i.e., upper and lower) surfaces of the second solid electrolytic sheet 65 interposed between the first chamber 11 and the first reference gas chamber 14.

The electrode 41 is integrally formed with the electrode 21 of the first electrochemical cell 2.

The third electrochemical cell 4 is connected to a voltmeter 451 so as to constitute a monitor circuit 45. A feedback circuit 455 is provided to control the power source 252 based on an output of the voltmeter 451.

The third electrochemical cell 4 functions as an oxygen sensing element capable of generating an electromotive force in response to an oxygen concentration. Thus, the third electrochemical cell 4 produces an output voltage representing the oxygen concentration in the first chamber 11.

The rest of the multilayered gas sensing element 18 is substantially identical with that of the multilayered gas sensing element 1 shown in FIG. 1, and therefore functions in the same manner and brings the same effects.

Third Embodiment

Figure 7:
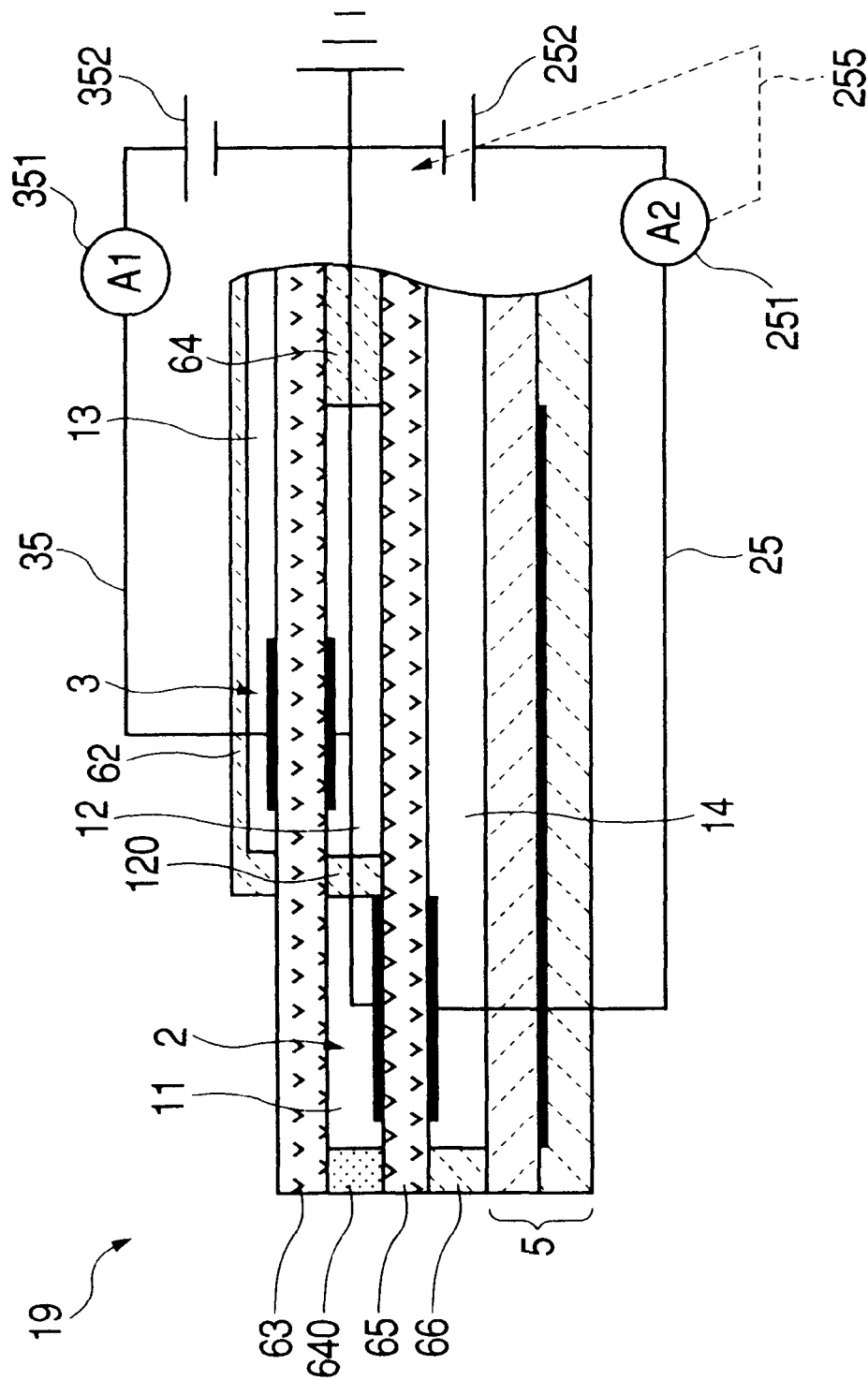
FIG. 7 is a cross-sectional view showing a multilayered gas sensing element in accordance with a third embodiment of the present invention.

FIG. 7 shows a multilayered gas sensing element 19 in accordance with a third embodiment of the present invention which differs from the multilayered gas sensing element 1 shown in FIG. 1 in that the objective gas is introduced from a different portion (i.e., side) to the first chamber 11.

As shown in FIG. 7, a porous member 640, as a part of the insulating sheet 64, is coupled between the first solid electrolytic sheet 63 and the second solid electrolytic sheet 65 so as to form a side wall of the first chamber 11. The objective gas to be measured is introduced into the first chamber 11 via the porous member 640. In this respect, the porous member 640 is functionally equivalent to the first diffusion resistive passage 110 shown in FIG. 1.

The rest of the multilayered gas sensing element 19 is substantially identical with that of the multilayered gas sensing element 1 shown in FIG. 1, and therefore functions in the same manner and brings the same effects.

Fourth Embodiment

Figure 8:
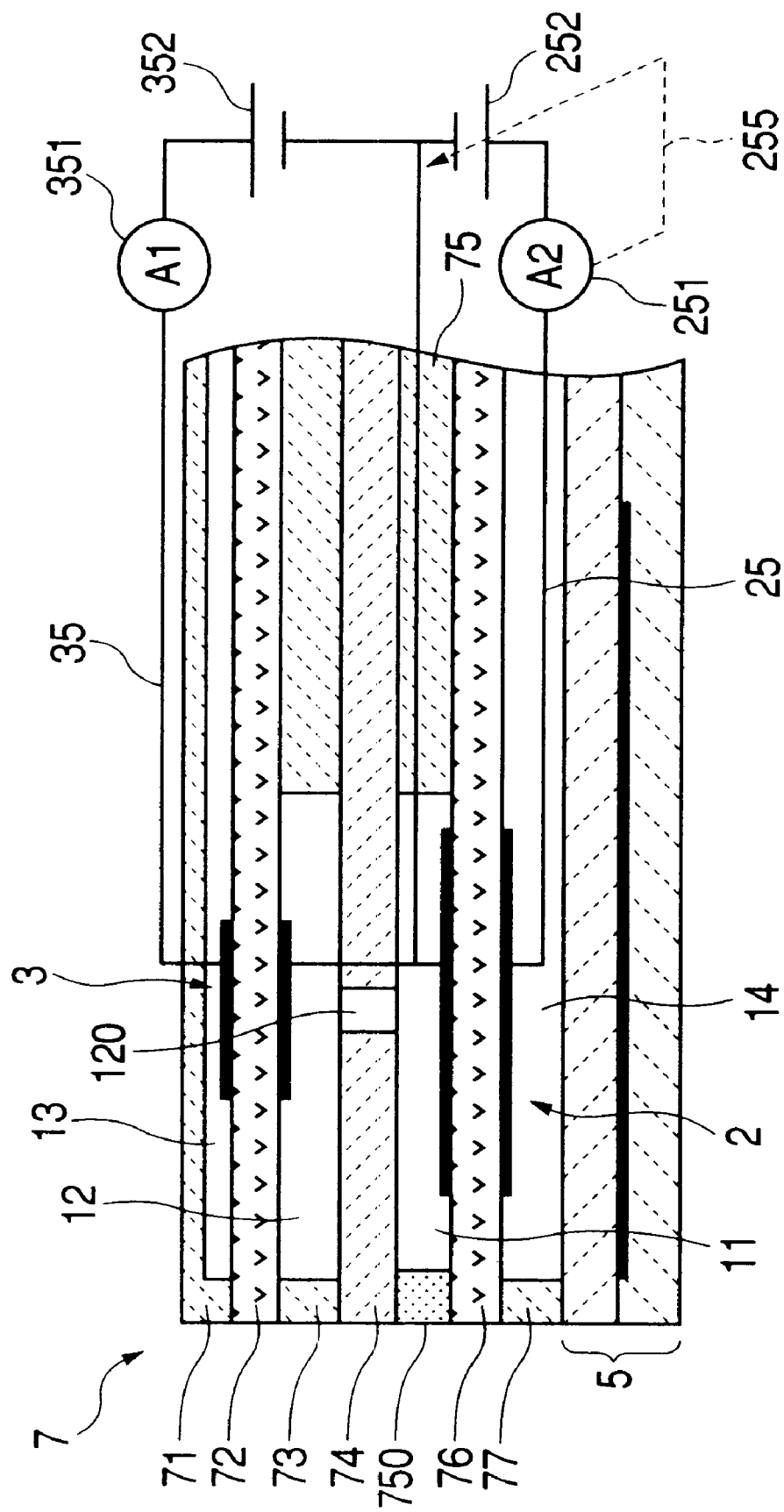
FIG. 8 is a cross-sectional view showing a multilayered gas sensing element in accordance with a fourth embodiment of the present invention.

FIG. 8 shows a multilayered gas sensing element 7 in accordance with a fourth embodiment of the present invention which is characterized in that all of the first chamber, the second chamber, the first reference gas chamber, and the second reference gas chamber are arrayed straight in the thickness direction (i.e., a direction perpendicular to the multilayered sheets) of the gas sensing element 7.

As shown in FIG. 8, the multilayered gas sensing element 7 of the fourth embodiment comprises a first solid electrolytic sheet 72, insulating sheets 73 and 74, an insulating sheet 75 comprising a porous member 750, a second solid electrolytic sheet 76, an insulating sheet 77, and a heater 5 which are successively stacked in this other. An insulating spacer 71 covers an outer surface of the first solid electrolytic sheet 72.

A second reference gas chamber 13 is formed between the insulating spacer 71 and the first solid electrolytic sheet 72.

More specifically, the second reference gas chamber 13 is defined by an inner recess of the insulating spacer 71 closed by the outer surface of the first solid electrolytic sheet 72. A first reference gas chamber 14 is defined in the insulating sheet 77 interposed between the second solid electrolytic sheet 76 and the heater 5.

A first chamber 11 is defined in the insulating sheet 75 interposed between the insulating sheet 74 and the second solid electrolytic sheet 76. A second chamber 12 is defined in the insulating sheet 73 interposed between the first solid electrolytic sheet 72 and the insulating sheet 74.

A second diffusion resistive passage 120 is a through hole opened across the insulating sheet 74 which connects the first chamber 11 to the second chamber 12. The objective gas to be measured is introduced into the first chamber 11 via the porous member 750. In this respect, the porous member 750 is functionally equivalent to the first diffusion resistive passage 110 shown in FIG. 1.

A first electrochemical cell 2 has a pair of electrodes located or provided on opposite (i.e., upper and lower) surfaces the second solid electrolytic sheet 76 interposed between the first chamber 11 and the first reference gas chamber 14.

A second electrochemical cell 3 has a pair of electrodes located or provided on opposite (i.e., upper and lower) surfaces the first solid electrolytic sheet 72 interposed between the second chamber 12 and the second reference gas chamber 13.

The rest of the multilayered gas sensing element 7 is substantially identical with that of the multilayered gas sensing element 1 shown in FIG. 1, and therefore functions in the same manner and brings the same effects.

Especially, the sensor arrangement of the fourth embodiment is advantageous in that the second electrochemical cell 3 can be positioned far from the first electrochemical cell 2 and the heater 5. Thus, the sensor output is accurate.

Fifth Embodiment

Figure 9:
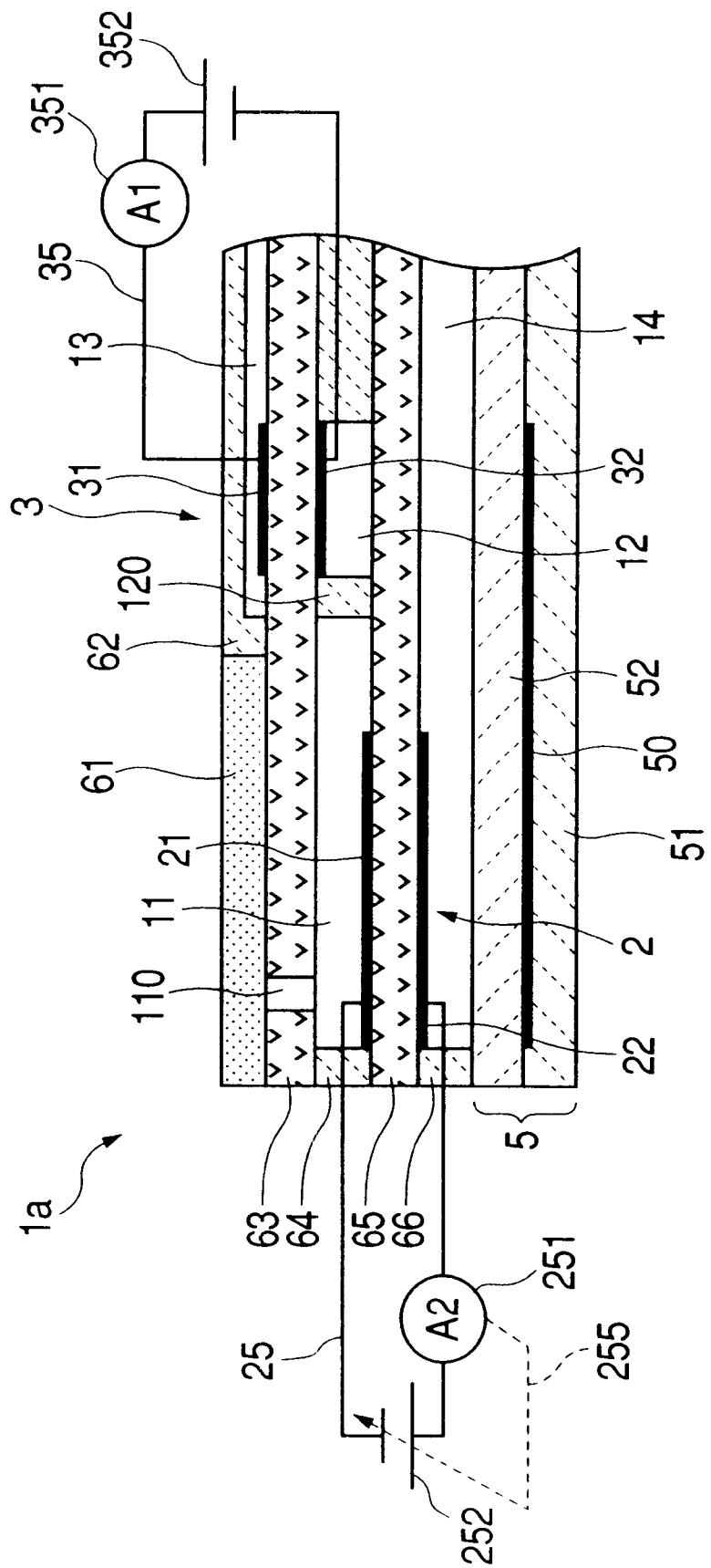
FIG. 9 is a cross-sectional view showing a multilayered gas sensing element in accordance with a fifth embodiment of the present invention.

FIG. 9 shows a multilayered gas sensing element 1a of the fifth embodiment comprising the first electrochemical cell 2 and the second electrochemical cell 3. The first electrochemical cell 2 has one end (i.e., electrode 21) provided in the first chamber 11 and the other end (i.e., electrode 22) provided in the first reference gas chamber 14. The second electrochemical cell 3 has one end (i.e., electrode 32) provided in the second chamber 12 and the other end (i.e., electrode 31) provided in the second reference gas chamber 13. The first electrochemical cell 2 and the second electrochemical cell 3 are provided on the solid electrolytic sheets 65 and 63 which are separately provided.

The first electrochemical cell 2 is connected to the ammeter 251 and the power source 252 so as to constitute the pump circuit 25. The feedback circuit 255, provided between the ammeter 251 and the power source 252, controls the voltage of power source 252 based on a current value of the ammeter 251, thereby causing the first electrochemical cell 2 to perform the oxygen pumping in and out operation.

Furthermore, the second electrochemical cell 3 is connected to the ammeter 351 and the power source 352 so as to constitute the sensor circuit 35. The ammeter 351 measures the oxygen ion current flowing across the second electrochemical cell 3.

The electrode 21 is inactive against NOx and therefore has no capability of decomposing NOx. On the other hand, the electrode 32 is active against NOx and therefore decomposes NOx into oxygen ions and nitrogen ion. Accordingly, the oxygen ion current obtained from the second electrochemical cell 3 is proportional to a NOx concentration. Thus, the NOx concentration can be known from the measured current value of ammeter 351.

According to the multilayered gas sensing element 1a of the fifth embodiment, the pump circuit 25 is provided independently of the sensor circuit 35. No leak current flows between the first electrochemical cell 2 and the second electrochemical cell 3. Thus, it becomes possible to ensure accurate measurement of the specific gas concentration.

The rest of the multilayered gas sensing element 1a is substantially identical with that of the multilayered gas sensing element 1 shown in FIG. 1, and therefore functions in the same manner and brings the same effects.

Sixth Embodiment

Figure 10:
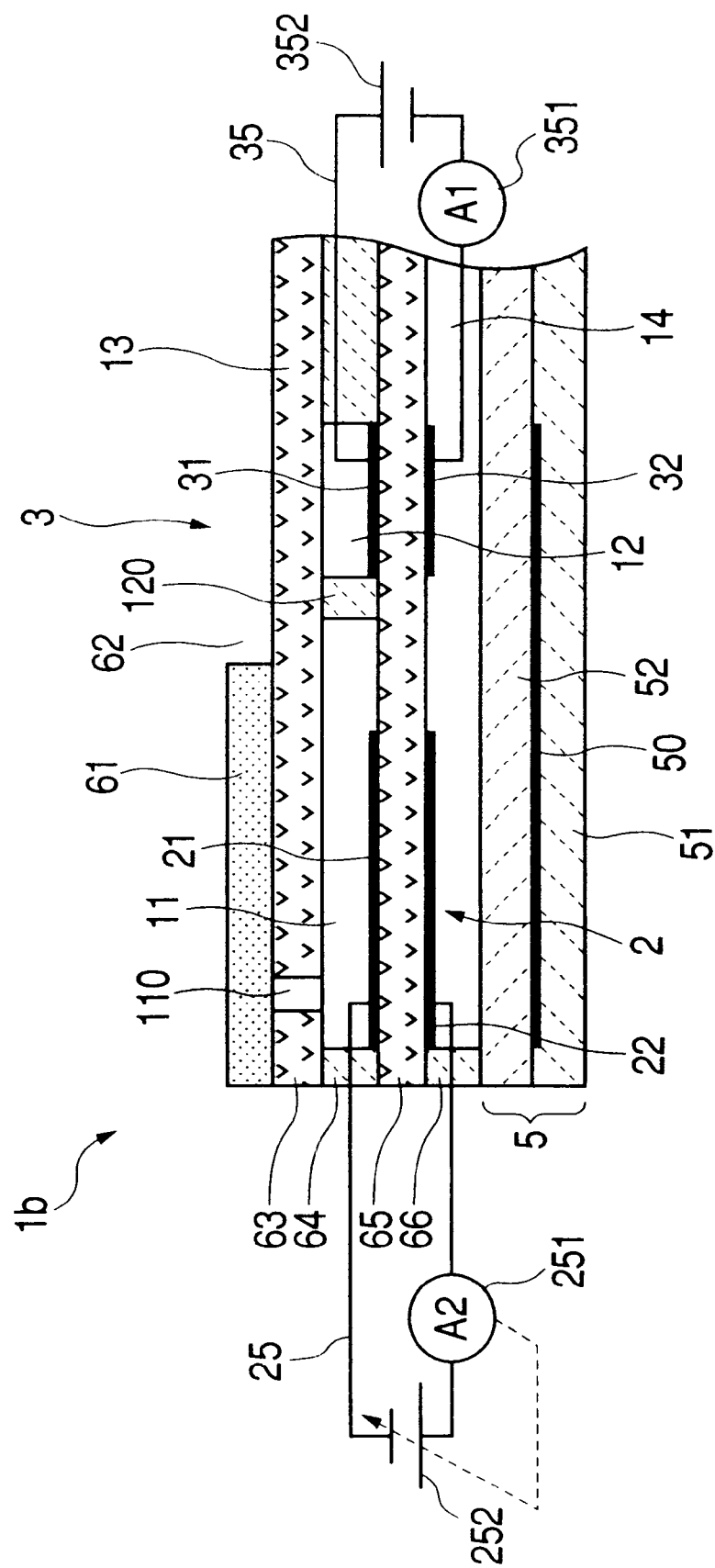
FIG. 10 is a cross-sectional view showing a multilayered gas sensing element in accordance with a sixth embodiment of the present invention.

FIG. 10 shows a multilayered gas sensing element 1b of the sixth embodiment which is characterized in that the same reference gas chamber 14 is used for the first electrochemical cell 2 and the second electrochemical cell 3. Namely, the electrode 22 of the first electrochemical cell 2 and the electrode 32 of the second electrochemical cell 3 are provided in the same reference gas chamber 14. Another reference gas chamber 13 is omitted.

The rest of the multilayered gas sensing element 1b is substantially identical with that of the multilayered gas sensing element 1 shown in FIG. 1, and therefore functions in the same manner and brings the same effects.

Seventh Embodiment

Figure 11:
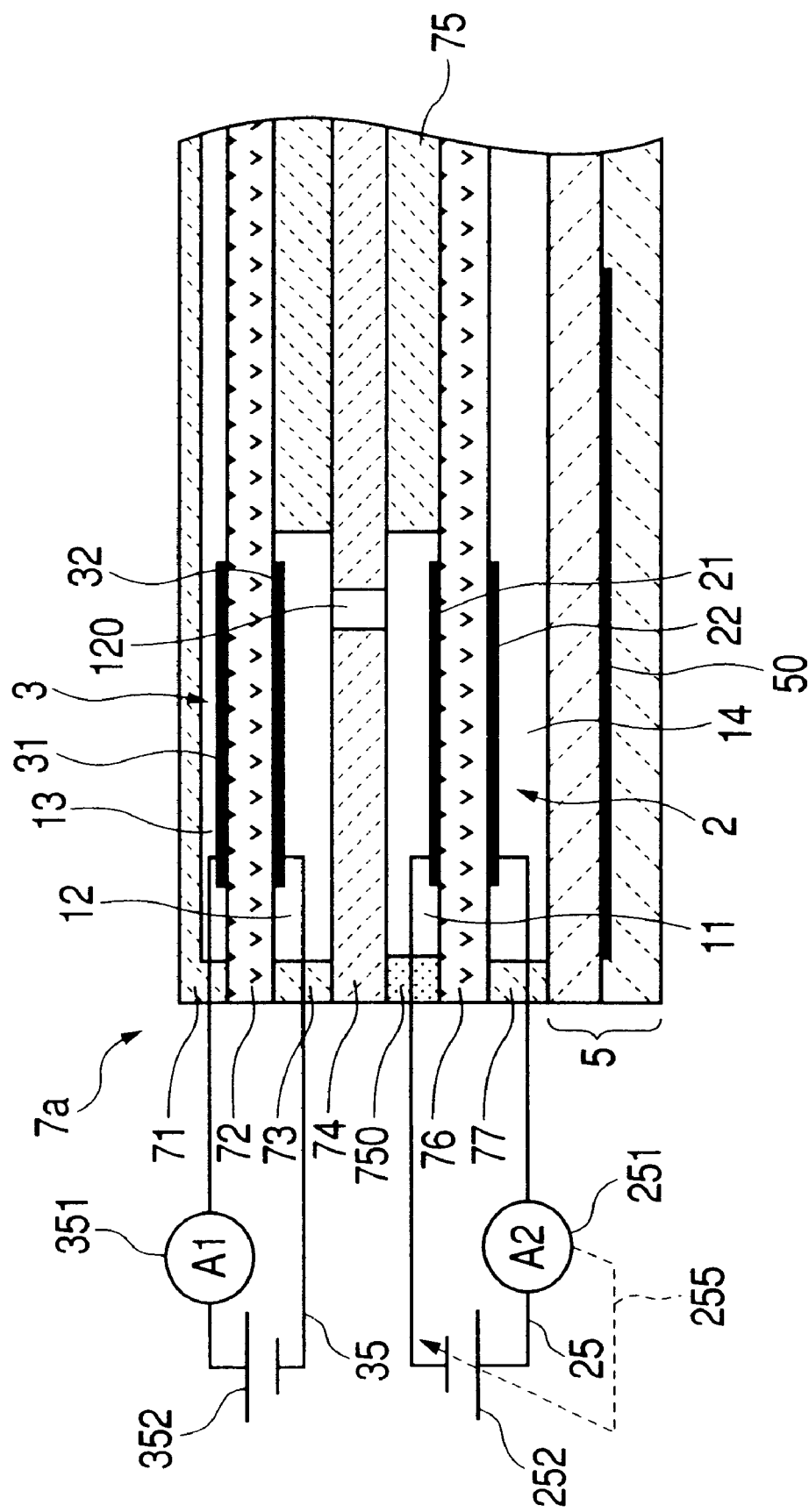
FIG. 11 is a cross-sectional view showing a multilayered gas sensing element in accordance with a seventh embodiment of the present invention.

FIG. 11 shows a multilayered gas sensing element 7a of the seventh embodiment which is characterized in that all of the first chamber, the second chamber, the first reference gas chamber, and the second reference gas chamber are aligned straight in the thickness direction (i.e., a direction perpendicular to the multilayered sheets) of the gas sensing element 7a.

As shown in FIG. 11, the multilayered gas sensing element 7a of the seventh embodiment comprises the first solid electrolytic sheet 72, the insulating sheets 73 and 74, the insulating sheet 75 comprising the porous member 750, the second solid electrolytic sheet 76, the insulating sheet 77, and the heater 5 which are successively stacked in this other. The insulating spacer 71 covers an outer surface of the first solid electrolytic sheet 72.

The second reference gas chamber 13 is formed between the insulating spacer 71 and the first solid electrolytic sheet 72. The first reference gas chamber 14 is defined in the insulating sheet 77 interposed between the second solid electrolytic sheet 76 and the heater 5.

The first chamber 11 is defined in the insulating sheet 75 interposed between the insulating sheet 74 and the second solid electrolytic sheet 76. The second chamber 12 is defined in the insulating sheet 73 interposed between the first solid electrolytic sheet 72 and the insulating sheet 74.

The second diffusion resistive passage 120 is a through hole opened across the insulating sheet 74 which connects the first chamber 11 to the second chamber 12. The objective gas to be measured is introduced into the first chamber 11 via the porous member 750. In this respect, the porous member 750 is functionally equivalent to the first diffusion resistive passage 110 shown in FIG. 1.

The first electrochemical cell 2 has a pair of electrodes located or provided on opposite (i.e., upper and lower)

surfaces the second solid electrolytic sheet 76 interposed between the first chamber 11 and the first reference gas chamber 14.

The second electrochemical cell 3 has a pair of electrodes located or provided on opposite (i.e., upper and lower) surfaces the first solid electrolytic sheet 72 interposed between the second chamber 12 and the second reference gas chamber 13.

According to the multilayered gas sensing element 7a of the seventh embodiment, the pump circuit 25 is provided independently of the sensor circuit 35. No leak current flows between the first electrochemical cell 2 and the second electrochemical cell 3. Thus, it becomes possible to ensure accurate measurement of the specific gas concentration.

The rest of the multilayered gas sensing element 7a is substantially identical with that of the multilayered gas sensing element 7 shown in FIG. 8, and therefore functions in the same manner and brings the same effects.

Especially, the sensor arrangement of the seventh embodiment is advantageous in that the second electrochemical cell 3 can be positioned far from the first electrochemical cell 2 and the heater 5. Thus, the sensor output is accurate.

Eighth Embodiment

Figure 12:
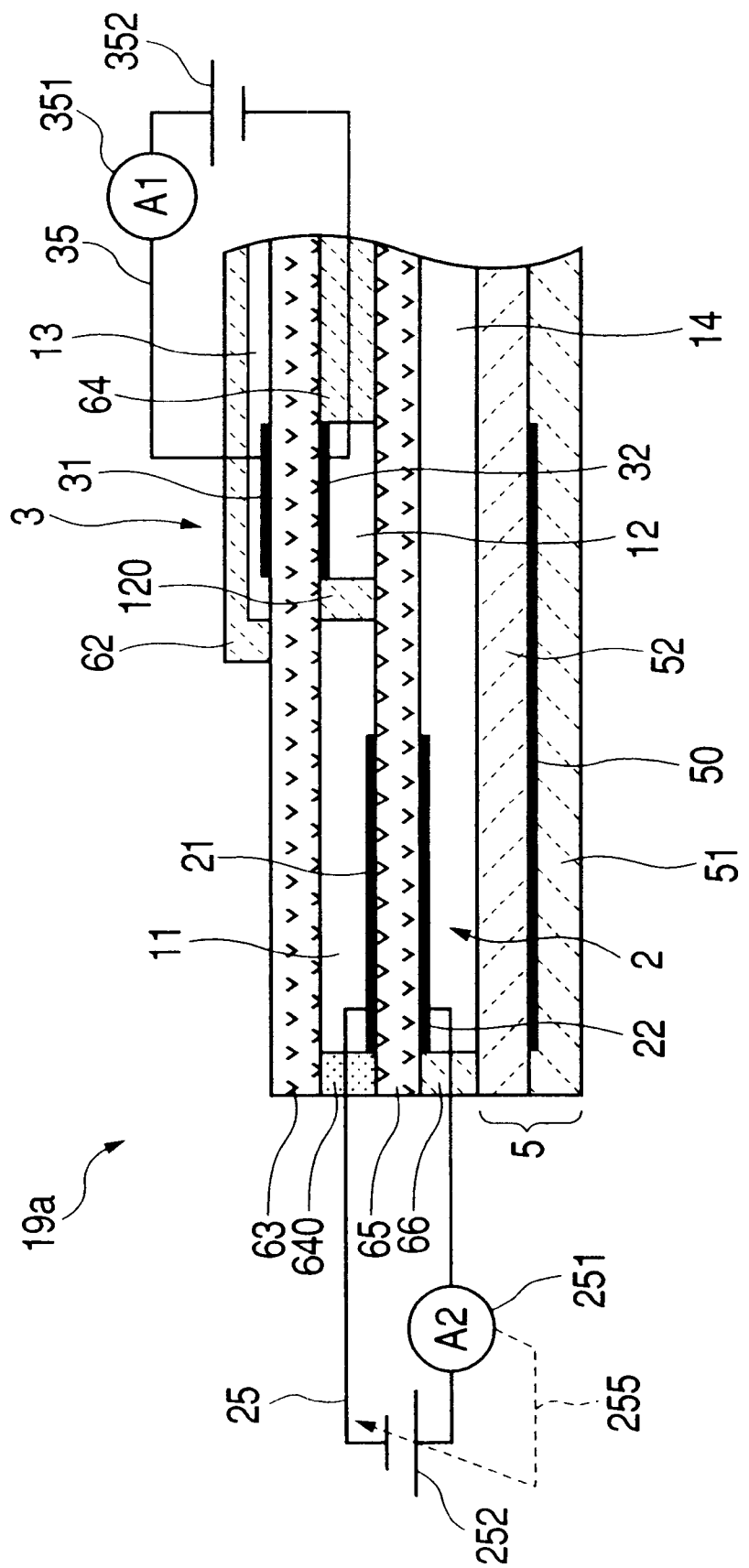
FIG. 12 is a cross-sectional view showing a multilayered gas sensing element in accordance with an eighth embodiment of the present invention.

FIG. 12 shows a multilayered gas sensing element 19a in accordance with an eighth embodiment of the present invention which differs from the multilayered gas sensing element 19 shown in FIG. 7 in that the pump circuit 25 is provided independently of the sensor circuit 35. No leak current flows between the first electrochemical cell 2 and the second electrochemical cell 3. Thus, it becomes possible to ensure accurate measurement of the specific gas concentration.

The rest of the multilayered gas sensing element 19a is substantially identical with that of the multilayered gas sensing element 19 shown in FIG. 7, and therefore functions in the same manner and brings the same effects.

Ninth Embodiment

Figure 13:
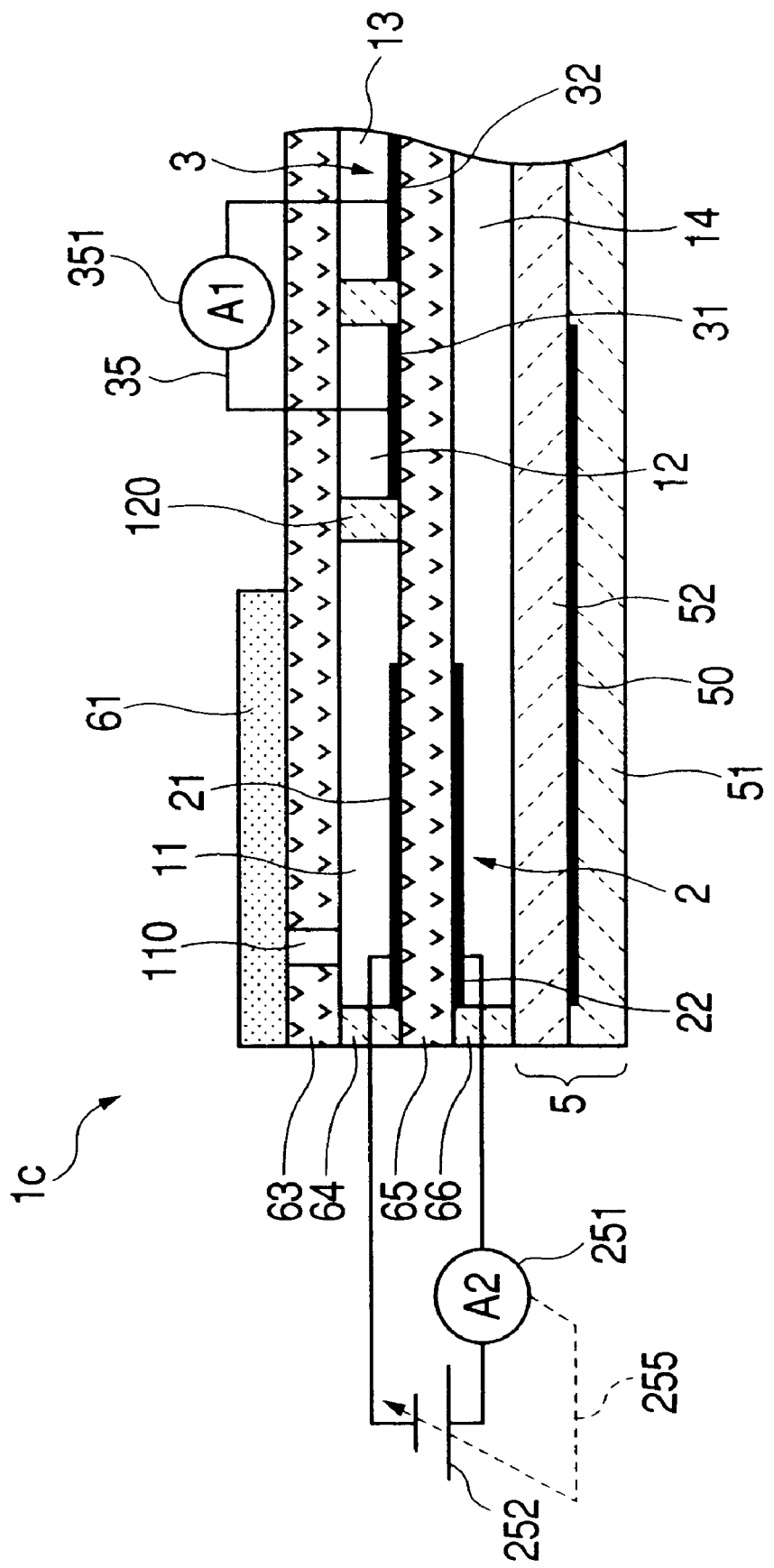
FIG. 13 is a cross-sectional view showing a multilayered gas sensing element in accordance with a ninth embodiment of the present invention.

FIG. 13 shows a multilayered gas sensing element 1c in accordance with a ninth embodiment of the present invention which is characterized in that, as well as the first chamber 11 and the second chamber 12, the second reference gas chamber 13 is defined in the first insulating sheet 64 interposed between the first solid electrolytic sheet 63 and the second solid electrolytic sheet 65. Thus, all of the first chamber 11, the second chamber 12, and the second reference gas chamber 13 are aligned straight in a direction parallel to the longitudinal direction of the multilayered sheets.

The electrodes 31 and 32 of the second electrochemical cell 3 are located on the same surface of the second solid electrolytic sheet 65.

The rest of the multilayered gas sensing element 1c is substantially identical with that of the multilayered gas sensing element 1 shown in FIG. 1, and therefore functions in the same manner and brings the same effects.

Tenth Embodiment

Figure 14:
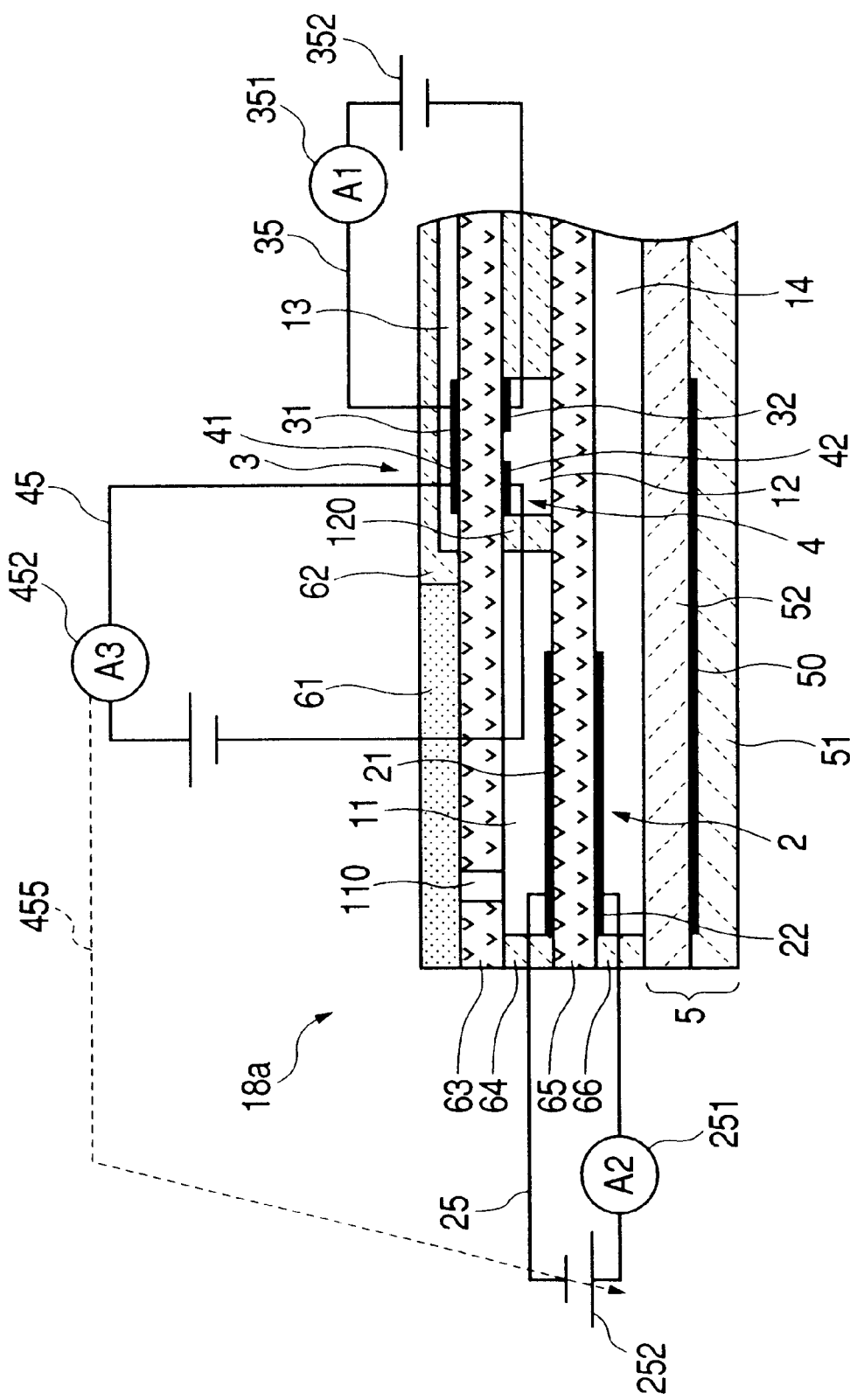
FIG. 14 is a cross-sectional view showing a multilayered gas sensing element in accordance with a tenth embodiment of the present invention.

FIG. 14 shows a multilayered gas sensing element 18a in accordance with a tenth embodiment of the present invention which has a third electrochemical cell 4 located or provided between the second chamber 12 and the second reference gas chamber 13. More specifically, the third electrochemical cell 4 comprises a pair of electrodes 41 and 42 located or provided on opposite (i.e., upper and lower) surfaces of the first solid electrolytic sheet 63 interposed between the second chamber 12 and the second reference gas chamber 13.

The electrode 41 is integrally formed with the electrode 31 of the second electrochemical cell 3.

The third electrochemical cell 4 is connected to an ammeter 452 SO as to constitute a monitor circuit 45. A feedback circuit 455 is provided to control the power source 252 based on a current value measured by the ammeter 452.

During operation of the multilayered gas sensing element 18a, the oxygen concentration in the second chamber 12 can be measured based on the current flowing across the third electrochemical cell 4. Based on the measured oxygen concentration, the voltage applied to the first electrochemical cell 2 can be controlled. Thus, the oxygen concentration in the second chamber 12 is stabilized. A stable sensor output is obtained.

The rest of the multilayered gas sensing element 18a is substantially identical with that of the multilayered gas sensing element 1 shown in FIG. 1, and therefore functions in the same manner and brings the same effects.

Eleventh Embodiment

Figure 15:
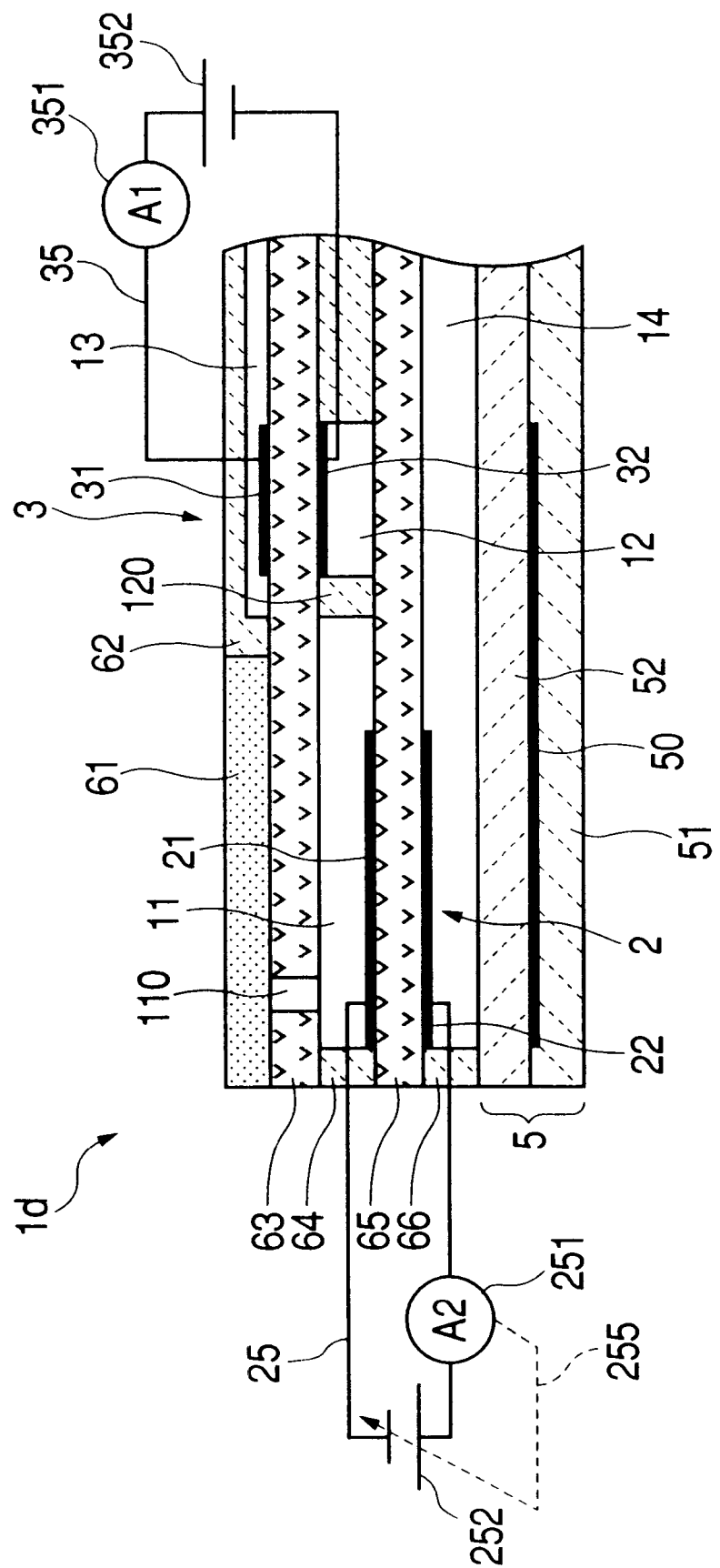
FIG. 15 is a cross-sectional view showing a multilayered gas sensing element in accordance with an eleventh embodiment of the present invention.

FIG. 15 shows a multilayered gas sensing element 1d in accordance with an eleventh embodiment of the present invention. The multilayered gas sensing element 1d comprises the first solid electrolytic sheet 63, the insulating sheet 64, the second solid electrolytic sheet 65, the insulating sheet 66, and the ceramic heater 5 which are stacked successively. The porous sheet 61 and the insulating spacer 62 cover the outer surface of the first solid electrolytic sheet 63. The heater 5 comprises the heater substrate 51 and the coating substrate 52.

All of these multilayered sheets are made of ZrO2.

The rest of the multilayered gas sensing element 1d is substantially identical with that of the multilayered gas sensing element 1a shown in FIG. 9, and therefore functions in the same manner and brings the same effects.

Twelfth Embodiment

Figure 16:
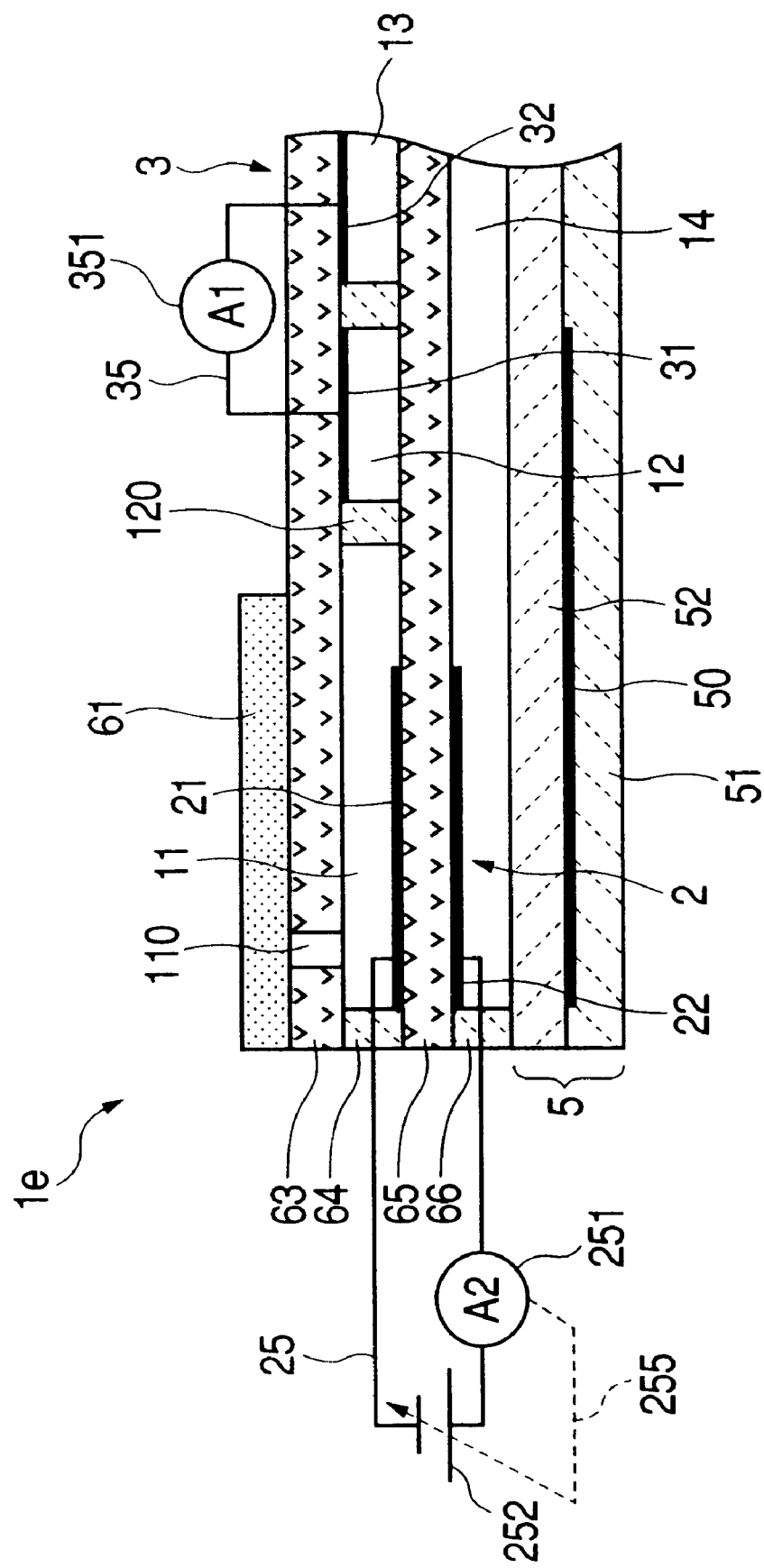
FIG. 16 is a cross-sectional view showing a multilayered gas sensing element in accordance with a twelfth embodiment of the present invention.

FIG. 16 shows a multilayered gas sensing element 1e in accordance with a twelfth embodiment of the present invention which is characterized in that, as well as the first chamber 11 and the second chamber 12, the second reference gas chamber 13 is defined in the first insulating sheet 64 interposed between the first solid electrolytic sheet 63 and the second solid electrolytic sheet 65. Thus, all of the first chamber 11, the second chamber 12, and the second reference gas chamber 13 are aligned straight in a direction parallel to the longitudinal direction of the multilayered sheets.

The electrodes 31 and 32 of the second electrochemical cell 3 are located on the same surface of the first solid electrolytic sheet 63.

The rest of the multilayered gas sensing element 1e is substantially identical with that of the multilayered gas sensing element 1 shown in FIG. 1, and therefore functions in the same manner and brings the same effects.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A multilayered gas sensing element comprising:

first and second chambers into which an objective gas to be measured is introduced;

a first diffusion resistive passage connecting said first chamber to an outside of said gas sensing element;

a second diffusion resistive passage connecting said first chamber to said second chamber;

a first electrochemical cell having one end located in said first chamber and the other end provided in a reference gas chamber for pumping in and out oxygen in accordance with an applied voltage;

a second electrochemical cell having one end located in said second chamber and being responsive to application of a predetermined voltage for generating a sensor current representing a specific gas concentration in said objective gas; and a heater incorporating a heat generating element capable of generating heat in response to current applied thereto, wherein an ion current path extending between said second electrochemical cell and said heat generating element is longer than an ion current path extending between said first electrochemical cell and said heat generating element.

2. The multilayered gas sensing element in accordance with claim 1, wherein said second electrochemical cell has the other end located in a reference gas chamber.

3. The multilayered gas sensing element in accordance with claim 2, wherein said reference gas chamber for said second electrochemical cell is formed separately from said reference gas chamber for said first electrochemical cell.

4. The multilayered gas sensing element in accordance with claim 1, wherein said heater has a base material made of alumina.

5. The multilayered gas sensing element in accordance with claim 1, wherein an insulating resistance between said second electrochemical cell and said heat generating element is larger than an insulating resistance between said first electrochemical cell and said heat generating element, and a minimum distance between said second electrochemical cell and said heat generating element is longer than a minimum distance between said first electrochemical cell and said heat generating element.

6. The multilayered gas sensing element in accordance with claim 1, wherein the insulating resistance between said second electrochemical cell and said heat generating element is equal to or larger than $1 \times 10^{12}$ Ω, leak current between said second electrochemical cell and said heat generating element is equal to or smaller than $2 \times 10^{-11}$ A, and the minimum distance between said second electrochemical cell and said heat generating element is equal to or larger than 0.4 mm.

7. The multilayered gas sensing element in accordance with claim 1, wherein said first electrochemical cell comprises a pair of electrodes provided on opposite surfaces of a first solid electrolytic sheet, and said second electrochemical cell comprises a pair of electrodes provided on opposite surfaces of a second solid electrolytic sheet which is different from said first solid electrolytic sheet.

8. The multilayered gas sensing element in accordance with claim 1, wherein an alumina sheet is disposed between said first electrochemical cell and said second electrochemical cell.

9. The multilayered gas sensing element in accordance with claim 1, wherein a third electrochemical cell is provided to measure an oxygen concentration in one of said first chamber and said second chamber.

10. The multilayered gas sensing element in accordance with claim 1, wherein said specific gas is NOx.

11. The multilayered gas sensing element in accordance with claim 1, wherein a minimum distance between said second electrochemical cell and said heat generating element is longer than a minimum distance between said first electrochemical cell and said heat generating element.

12. The multilayered gas sensing element in accordance with claim 11, wherein the minimum distance between said second electrochemical cell and said heat generating element is equal to or larger than 0.4 mm.

13. The multilayered gas sensing element in accordance with claim 12, wherein the minimum distance between said second electrochemical cell and said heat generating element is equal to or less than 10 mm.

14. The multilayered gas sensing element in accordance with claim 1, wherein the insulating resistance between the second electrochemical cell and the heat generating element is larger than an insulating resistance between the first electrochemical cell and the heat generating element.

15. The multilayered gas sensing element in accordance with claim 14, wherein the insulating resistance between the second electrochemical cell and the heat generating element is equal to or larger than $1 \times 10^{12}$ Ω.

16. The multilayered gas sensing element in accordance with claim 1, wherein a current flowing from the heat generating element to the second electrochemical cell is equal to or smaller than $2 \times 10^{-11}$ A.

* * * * *